United States Patent
Saunthararajah et al.

(10) Patent No.: US 11,779,591 B2
(45) Date of Patent: Oct. 10, 2023

(54) COMPOSITIONS CONTAINING DECITABINE, 5AZACYTIDINE AND TETRAHYDROURIDINE AND USES THEREOF

(71) Applicant: Epidestiny, Inc., Solon, OH (US)

(72) Inventors: Yogen Saunthararajah, Cleveland, OH (US); Joseph Desimone, Glen Ellyn, IL (US); Henry Lau, Martinsville, NJ (US); Santhosh Vadivelu, Solon, OH (US)

(73) Assignee: EPIDESTINY, INC., Solon, OH (US)

( * ) Notice: Subject to any disclaimer, the term of this patent is extended or adjusted under 35 U.S.C. 154(b) by 0 days.

(21) Appl. No.: 17/586,387

(22) Filed: Jan. 27, 2022

(65) Prior Publication Data
US 2022/0152075 A1   May 19, 2022

Related U.S. Application Data

(62) Division of application No. 15/780,796, filed as application No. PCT/US2016/064935 on Dec. 5, 2016, now Pat. No. 11,376,270.

(60) Provisional application No. 62/429,292, filed on Dec. 2, 2016, provisional application No. 62/262,839, filed on Dec. 3, 2015.

(51) Int. Cl.
*A61K 31/7068* (2006.01)
*A61P 35/02* (2006.01)
*A61K 9/00* (2006.01)
*A61K 31/706* (2006.01)

(52) U.S. Cl.
CPC ........ *A61K 31/7068* (2013.01); *A61K 9/0053* (2013.01); *A61K 31/706* (2013.01); *A61P 35/02* (2018.01)

(58) Field of Classification Search
CPC ...... A61K 2300/00; A61P 35/00; A61P 35/02; A61P 7/00
See application file for complete search history.

(56) References Cited

U.S. PATENT DOCUMENTS

| | | |
|---|---|---|
| 6,596,859 B1 | 7/2003 | Abushanab et al. |
| 7,144,873 B2 | 12/2006 | Joshi-Hangal et al. |
| 8,158,770 B2 | 4/2012 | Wedekind et al. |
| 8,329,665 B2 | 12/2012 | Belyakov et al. |
| 8,399,420 B2 | 3/2013 | Silverman et al. |
| 8,618,075 B2 | 12/2013 | Hamilton et al. |
| 8,841,277 B2 | 9/2014 | Nguyen et al. |
| 8,846,628 B2 | 9/2014 | Etter et al. |
| 8,987,220 B2 | 3/2015 | Eilertsen |
| 9,259,469 B2 | 2/2016 | Desimone et al. |
| 9,265,785 B2 * | 2/2016 | Desimone .......... A61K 31/7072 |
| 9,567,363 B2 | 2/2017 | Hamilton et al. |
| 9,895,391 B2 | 2/2018 | Desimone et al. |

| | | |
|---|---|---|
| 2005/0056280 A1 | 3/2005 | Alston et al. |
| 2010/0062992 A1 | 3/2010 | Redkar et al. |
| 2014/0100182 A1 | 4/2014 | Labhasetwar et al. |
| 2014/0186335 A1 | 7/2014 | Hamilton et al. |
| 2014/0221305 A1 | 8/2014 | Belyakov et al. |

FOREIGN PATENT DOCUMENTS

| | | |
|---|---|---|
| CN | 101827856 A | 9/2010 |
| CN | 102037003 A | 4/2011 |
| CN | 102485232 A | 6/2012 |
| CN | 103338753 A | 10/2013 |
| CN | 103782167 A | 5/2014 |
| EP | 1156827 A2 | 11/2001 |
| EP | 1819227 A1 | 8/2007 |
| EP | 2381780 A1 | 11/2011 |
| EP | 2416780 A1 | 2/2012 |
| EP | 2447272 B2 | 2/2017 |
| WO | 2001051639 A2 | 7/2001 |
| WO | 2006037024 A2 | 4/2006 |
| WO | 2006071491 A1 | 7/2006 |
| WO | 2006099132 A1 | 9/2006 |
| WO | 2009052287 A1 | 4/2009 |
| WO | 2010075301 A1 | 7/2010 |
| WO | 2010118010 A1 | 10/2010 |
| WO | 2014025582 A1 | 2/2014 |
| WO | 2014143051 A1 | 9/2014 |
| WO | 2017158396 A1 | 9/2017 |

OTHER PUBLICATIONS

Ebrahem et al., High cytidine deaminase expression in the liver provides sanctuary for cancer cells from decitabine treatment effects, Oncotarget 3(10):1137-1145 (2012).
Desimone et al., "Tetrahydrouridine, Cytidine Analogues, and Hemoglobin F", American Journal of Hematology 18: 283-288 (1985).
Dover et al. "5-Azacytidine increases HbF production and reduces anemia in sickle cell disease: dose-response analysis of subcutaneous and oral dosage regimens." 1 527-532 (1985).
Ferraris et al., "Design, Synthesis, and Pharmacological Evaluation of Fluorinated Tetrahydrouridine Derivatives as Inhibitors of Cytidine Deaminase", J Med Chem. 57(6): 2582-2588 (2014).
Gilbert et al., "Gemcitabine Pharmacogenomics: Cytidine Deaminase and Deoxycytidylate Deaminase Gene Resequencing and Functional Genomics", Clin. Cancer Res. 12(6): 1794-1803 (2006).
Hubeek et al., "The human equilibrative nucleoside transporter I mediates in vitro cytarabine sensitivity in childhood acute myeloid leukaemia", Br. J. Cancer, 93: 1388-1394 (2005).

(Continued)

*Primary Examiner* — Pancham Bakshi
(74) *Attorney, Agent, or Firm* — Nixon Peabody LLP; Ravinderjit Braich

(57) ABSTRACT

Compositions comprising decitabine and tetrahydrouridine or 5-azacytidine and tetrahydrouridine for the treatment of cancer are disclosed. The compositions in the form of a pill is administered to a human subject sequentially or alternately guided by the measurement of predictive biomarkers.

15 Claims, 10 Drawing Sheets

(56) References Cited

OTHER PUBLICATIONS

Huang et al., "Membrane Transporters and Channels: Role of the Transportome in Cancer Chemosensitivity and Chemoresistance", Cancer Res. 64: 4294-4301 (2004).

Kelly et al., "Pharmacokinetic Considerations in Evaluating the Effects of Tetrhydrouridine on 5-Azacytidine Chemotherapy in LI210 Leukemic Mice", Cancer Treatment Reports, 62(7): 1025-1032 (1978).

Kirch et al., "Recombinant gene products of two natural variants of the human cytidine deaminase gene confer different deamination rates of cytarabine in vitro", Exp. Hematol. 26(5): 421-425 (1998).

Lavelle et al., "Effects of tetrahydrouridine on pharmacokinetics and pharmacodynamics oforal decitabine," Blood 119(5): 1240-1247 (2012).

Liu et al., "Characterization of decomposition products and preclinical and low dose clinical pharmacokinetics of decitabine (5-aza-2'-deoxycytidine) by a new liquid chromatography/tandem mass spectrometry quantification method", Rapid Common Mass Spectrum, 20: 1117-1126 (2006).

Molokie et al., ""Oral tetrahydrouridine and decitabine for non-cytotoxic epigenetic gene regulation in sickle cell disease: A randomized phase 1 study"", PLos MED, 14(9):el002382 (28 pages) (2017).

Momparler et al., "Comparison of the antileukemic Activity of 5-aza-2'-deoxycytidine, 1-?-D-arabinofuranosylcytosine and 5-azacytidine against LI210 leukemia", Leukemia Research, 8(6): 1043-1049 (1984).

Negrotto et al. "Noncytotoxic Differentiation Treatment of Renal Cell Cancer", Cancer Res. 71(4): 1431-1441 (2011).

Neil et al. "Enhancement by tetrahydrouridine (NSC-112907) of the oral activity of 5-azacytidine (NSC-102816) in L1210 leukemic mice." Cancer Chemotherapy Reports 59(3): 459-465 (1975).

Norton et al. "Synthesis of Deoxytetrahydrouridine", J. Org. Chem., 74(5): 2221-2223 (2009).

Ohta et al., "Impact of cytidine deaminase activity on intrinsic resistance to cytarabine in carcinoma cells", Oncol. Rep. 12: 1115-1120 (2004).

Terse et al. "Subchronic oral toxicity study of decitabine in combination with tetrahydrouridine in CD-1 mice." International journal of toxicology 33(2): 75-85 (2014).

Yue et al., "A functional single-nucleotide polymorphism in the human cytidine deaminase gene contributing to ara-C sensitivity", Pharmacogenetics, 13: 29-38 (2003).

International Search Report in International Patent Application No. PCT/US2016/064935, dated Mar. 13, 2017 (5 pages).

Written Opinion in International Patent Application No. PCT/US2016/064935, datwd Mar. 13, 2017 (7 pages).

FDA "Guidance for Industry Estimating the Maximum Safe Starting Dose in Initial Clinical Trials for Therapeutics in Adult Healthy Volunteers" pp. 1-27 (2005).

\* cited by examiner

Fig. 2. PBRM1 is 2nd only to VHL as the most commonly inactivated gene in RCC. The mesenchymal-epithelial differentiation driver PAX8 is amplified.

Fig.3. WT1 promoter CpG are hypermethylated in RCC (blue) compared to paired non-cancerous kidney (orange)

Fig.4. High expression in RCC of differentiation drivers (PAX8, PAX2), yet, paradoxically, epigenetic repression of key epithelial differentiation target genes (e.g., WT1, GATA3).

Fig 6. DNMT1 depletion by non-cytotoxic concentrations of decitabine (DAC) shifts PAX8 interactions towards coactivators (green) and away from corepressors (red).

LC/MSMS. SKRC45 RCC cells were treated with vehicle or Dec (DAC). Western blot confirmation was done for representatives of multiple complexes.

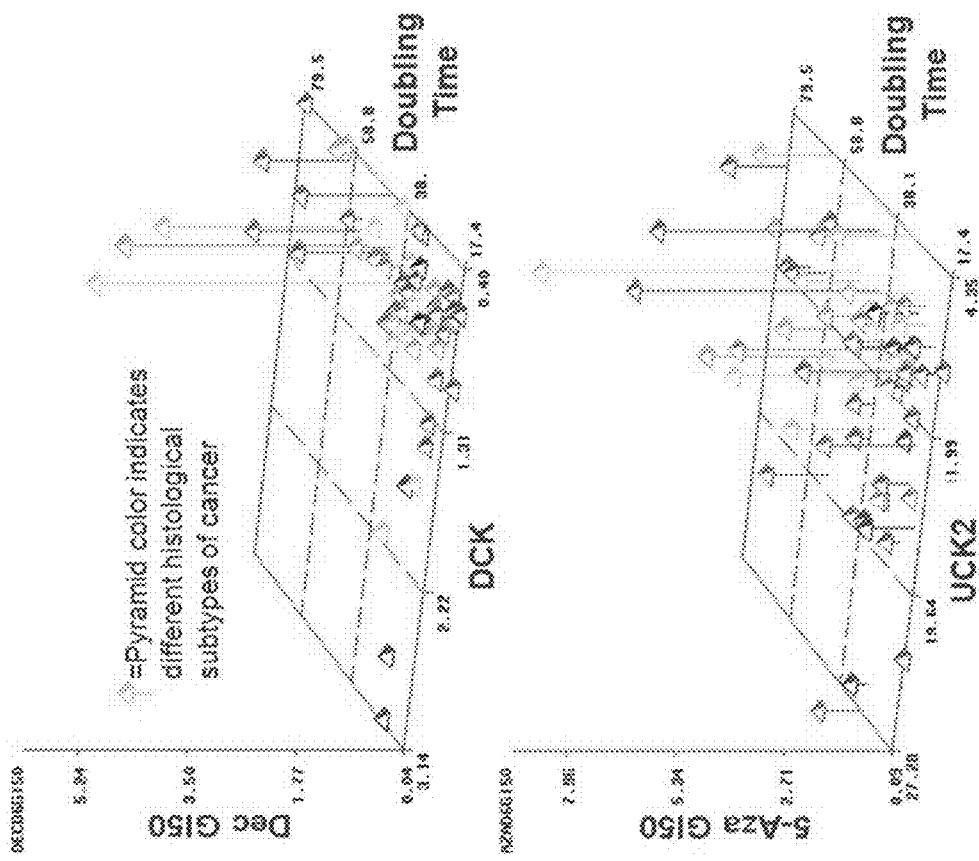

Fig. 7. DCK and UCK2 expression levels correlate with Dec and 5Aza sensitivity respectively, demonstrating the critical role of enzyme determinants of intra-cellular half-life, and also doubling time/S-phase fraction, to the activity of these S-phase specific drugs that deplete a pan-cancer relevant molecular target, DNMT1. Analysis is of cell lines representative of the histologic and genetic diversity of cancer (NCI60), GI50: the drug concentration resulting in a 50% growth reduction. (raw data downloaded from NCI DTP - http://dtp.nci.nih.gov and GSE5846).

Figure 7

Fig.8. At relapse, MDS/AML cells from patients treated with Dec have lower DCK and higher UCK2, and vice-versa in 5Aza treated patients (this matches *in vitro* observations and predictions by several groups)

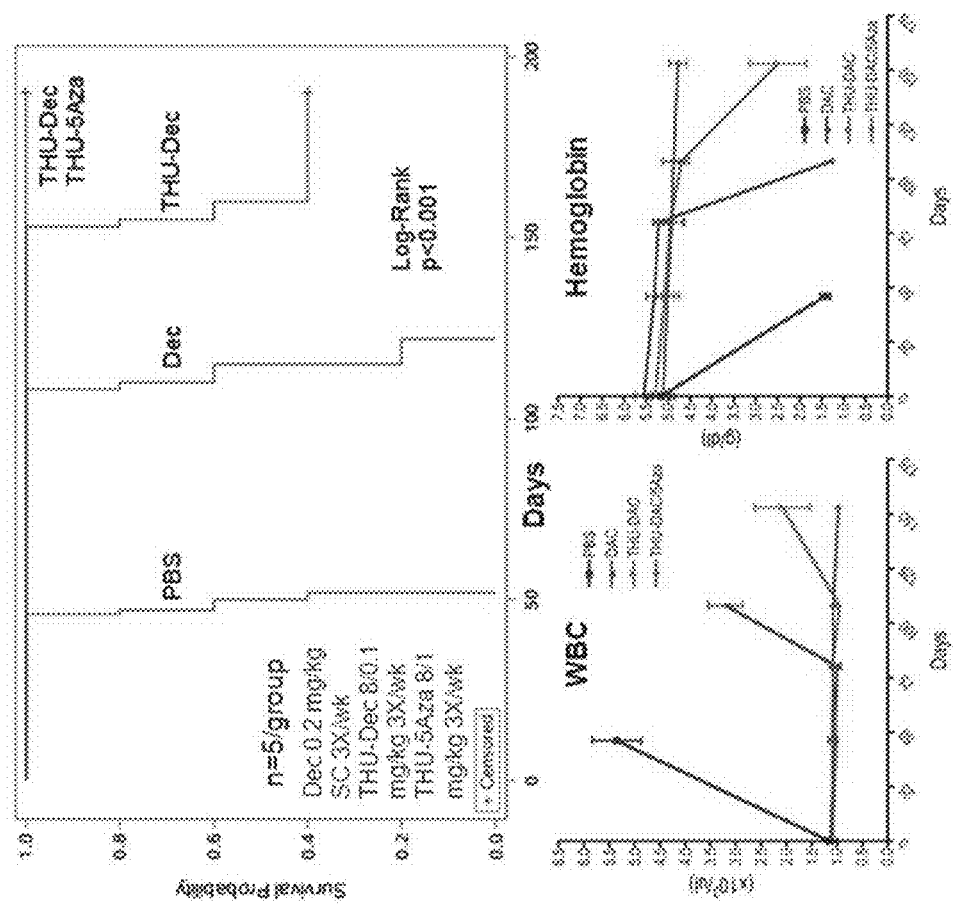

Fig. 9. THU-Dec 3X/wk alternating with THU-5Aza 3X/wk (THU-Dec/THU-5Aza) is producing remarkable efficacy in xenotransplant models of patient-derived AML. The dosages and schedules of drug are non-cytotoxic[1,2], and preserve marrow function, facilitating sustainable therapy (anemia is caused by progressive leukemia (↑WBC), not treatment). THU-5Aza alone was equivalent to THU-Dec alone (previous expt., data not shown)

COMPOSITIONS CONTAINING DECITABINE, 5AZACYTIDINE AND TETRAHYDROURIDINE AND USES THEREOF

RELATED APPLICATIONS DATA

This application is a divisional under 35 U.S.C. § 121 of co-pending U.S. application Ser. No. 15/780,796 filed Jun. 1, 2018, now U.S. Pat. No. 11,376,270 issued Jul. 5, 2022, which is a 35 U.S.C. § 371 National Phase Entry Application of International Application No. PCT/US16/64935 filed Dec. 5, 2016, which designates the U.S. and which claims the benefit under 35 U.S.C. § 119(e) from U.S. Provisional Application Ser. No. 62/262,839 filed Dec. 3, 2015 and Ser. No. 62/429,292 filed Dec. 2, 2016.

FIELD OF THE INVENTION

This application relates generally to compositions containing decitabine (DEC), 5-azacytidine (5AZA) and tetrahydrouridine (THU) and the methods of using the compositions for the treatment of cancers and blood disorders in a subject. Specifically, the compositions in the form of a pill include DEC and THU or 5AZA and THU or a combination of DEC, 5AZA and THU as a non-cytotoxic treatment for cancer or other blood disorders in a subject.

BACKGROUND OF THE INVENTION

Radiation and drug treatments for cancer intend to engage physiologic pathways that can terminate growth and division of cells. The specific physiologic pathway that almost all cancer drugs are attempting to engage is the p53/p16-mediated apoptosis pathway (cytotoxicity). Since p53 and p16 are the two most commonly inactivated genes in cancer, this p53/p16-dependence of cancer drugs and radiation is a fundamental basis for treatment resistance and relapse. Hence there is a need for novel treatment approaches that do not use the p53/p16 system to terminate the cell growth and division of cancer cells.

Pre-clinical and clinical studies have shown that non-cytotoxic depletion of the enzyme DNA methyl transferase 1 (DNMT1) by decitabine (DEC) and 5-azacytidine (5AZA) could be an effective form of treatment that does not require or rely on the p53/p16 system (Negrotto S., et al. 2011 Cancer Res 71(4):1431-1441). Yet 5AZA or DEC by themselves are not curative, neither in pre-clinical in vivo models of cancer nor in the clinic. It would therefore be desirable to utilize mechanisms of cancer resistance to p53-independent treatment with 5AZA or DEC.

SUMMARY OF THE INVENTION

The present disclosure has identified that cancer resistance to p53-independent treatment with 5AZA or DEC can be effectively overcome by logical, non-toxic and clinically applicable solutions. Specifically, the present disclosure provides compositions of non-cytotoxic THU-DEC/THU-5AZA and methods for overcoming cancer resistance by administration of compositions comprising non-cytotoxic levels of THU-DEC and administering the composition in an alternating regimen i.e., alternating the intake of the composition that may be in the form of a pill or tablet containing THU-DEC and THU-5AZA for defined time periods.

Accordingly, in one embodiment an oral composition for inducing safe, non-cytotoxic (p53/p16-independent) differentiation-mediated cell cycle exits of cancer cells is provided.

The composition for oral administration comprising a nucleoside analog drug that can bind irreversibly and deplete the enzyme DNA methyl transferase 1 (DNMT1), a potent cytidine deaminase (CDA) inhibitor and one or more pharmaceutically acceptable excipients, wherein the nucleoside analog drug and the potent cytidine deaminase inhibitor are present in therapeutically effective amounts sufficient to induce differentiation of a refractory and resistant cancer cell without cytotoxicity to normal tissues. The nucleoside analog drug that deplete the DNMT1 enzyme present in the composition is DEC. The nucleoside analog drug in one embodiment may also be 5AZA. The CDA inhibitor in the composition may be tetrahydrouridine (THU) or certain tetrahydrouridine derivatives such as 2'-fluorinated tetrahydrouridine derivatives. In this embodiment when the nucleoside analog drug that deplete DNMT1 is DEC it may be present in amounts ranging from 1-10 $mg/m^2$. When the nucleoside analog drug present in the oral composition is 5AZA it may be present in amounts ranging from 10-100 $mg/m^2$. The CDA inhibitor THU in the oral composition may be present in amounts ranging from about 400 $mg/m^2$ to about 500 $mg/m^2$.

A treatment composition for inducing non cytotoxic differentiation may exist in the form of a pill or tablet or capsule. The treatment composition in one embodiment may comprise the nucleoside analog drug DEC and THU and one or more pharmaceutically acceptable carriers. The treatment composition in another embodiment may comprise 5AZA, THU and one or more pharmaceutically acceptable carriers. The treatment composition in some embodiment may comprise a therapeutically effective amount of both of the nucleoside analog drugs (DEC or 5AZA) combined with THU in a single pill.

The treatment composition may be administered to a subject after measurement of a predictive biomarker, including but not limited to DCK in the cancer cells. Development of predictive biomarkers may assist a treating physician to select the right treatment regimen in order to be more effective in treating an especially refractory and aggressive metastatic cancer in a subject. In this embodiment the predictive biomarker may be the pyrimidine metabolism enzyme deoxycytidine kinase (DCK) of cancer cells. The DCK enzyme is known to phosphorylate and trap DEC in cells and several cancer cells avoid the DEC-induced DNMT-1 depletion by resorting to an alternative pyrimidine metabolism enzyme UCK2, which however renders the cancerous cells vulnerable to the drug 5-5AZA. The measurement of DCK of cancer cells may be performed before or during or after administration of the oral composition by functional molecular imaging with—positron emission tomography (PET) utilizing a DCK-dependent probe or by QRT-PCR.

In a treatment method for inducing non cytotoxic differentiation of cancer cells in any mammalian tissue, a first treatment composition comprising DEC, THU and one or more pharmaceutically acceptable carriers and a second treatment composition comprising 5-5AZA, THU and one or more pharmaceutically acceptable carriers may each be administered to a patient in need thereof sequentially or alternately or simultaneously. In this embodiment the tetrahydrouridine may also include derivatives such as the 2'-fluorinated tetrahydrouridine derivatives. The first and the second compositions may be administered after, or during or before measuring the predictive biomarkers in cancer cells.

In one embodiment the first and the second treatment compositions may each be in the form of a pill or they may be combined within a single pill. When the compositions of the present disclosure exist in the form of a pill the THU or the THU derivative may specifically be located on the surface of the pill, while the DEC or 5AZA may be located inside the pill. Such differential location of the nucleoside analog drugs, DEC or 5AZA and the THU on a pill may ensure that the THU or the THU derivative may be bioavailable about 1 minute to 180 minutes or 15 minutes to about 180 minutes before either DEC or 5AZA and more preferably between 30 to about 60 minutes before either DEC or 5AZA. In another embodiment the DEC or 5AZA may be coated or embedded in a polymer to facilitate a delayed release of the drugs compared to the release of a polymer coated or embedded THU or THU derivative.

Upon oral administration of the treatment composition the combination of DEC and THU may produce at least about 10-fold improvement in the oral bioavailability, low $C_{max}$ and multi-hour $T_{max}$ needed for non-cytotoxic DNMT-1 depletion by DEC or 5AZA. Because of known off-target or toxic effects of DEC and 5AZA, optimizing DEC or 5AZA to deplete DNMT1 in vivo may have powerful therapeutic benefits. Accordingly, the treatment composition may result in a peak plasma DEC level of about 0.05 µm to about 0.5 µm in a human subject, or a peak plasma 5AZA level of about 0.5 to about 5 µm. In this embodiment a treating physician may prescribe a pill containing DEC and THU (or) -5AZA and THU in a sequential or intermittent fashion in such a way that the patient stricken with cancer takes a pill containing DEC and THU first followed by days or weeks apart by a pill containing 5AZA and THU or vice versa.

In one embodiment a method for treating any tumor, metastatic tumor or combination thereof in a tissue of a subject or blood malignancies or blood disorders in a subject is provided. The method comprising the steps of (i) administering a therapeutically effective amount of a first composition in the form of a pill comprising a first nucleoside analog drug, a cytidine deaminase inhibitor and a pharmaceutically acceptable carrier, (ii) administering a second composition in the form of a pill comprising a second nucleoside analog drug, a cytidine deaminase inhibitor and a pharmaceutically acceptable carrier, wherein the nucleoside analog drug in the first composition may be DEC, the nucleoside analog drug in the second composition may be 5AZA and the cytidine deaminase inhibitor in the said first composition and the said second composition is THU or THU derivative such as 2'-fluorinated tetrahydrouridine derivatives. In this embodiment the first and the second compositions may be administered sequentially or alternately or simultaneously. Additionally, the first and second compositions may be administered before or during or after measuring the level of predictive biomarker in the cancer cells of a subject.

A treatment selection involves the determination of the DCK level in a patient requiring treatment and prescribing the appropriate nucleoside analog drug in combination with THU (i.e., DEC and THU or 5AZA and THU or both) in such a way to steer the cancerous tissue towards a differentiation pathway. The drug compositions in the form of a pill may be prescribed once a week or once every two weeks or between once to three times per week to patients stricken with cancer or blood malignancies or disorders. In yet other embodiment, the composition in the form of a pill may be prescribed between once every two weeks to as often as three times per week in patients at risk of developing hematological or solid malignancy, or at risk of having a relapse in a previous diagnosis of hematological or solid malignancy or hematological or blood disorders.

In one embodiment a kit for treating a tumor or refractory tumor or hematological tumor or blood disorders is provided. The kit may comprise: (i) a pill comprising DEC, THU or THU derivative and a carrier, (ii) a pill comprising 5AZA, THU or THU derivative and a carrier and (ii) an instruction manual. In another embodiment the kit may comprise (i) a capsule comprising a mixture of DEC/THU microspheres or microparticles and 5AZA/THU microspheres or microparticles and (ii) an instruction Manual. The pill or capsule may be formulated in such a way that THU or THU derivative is always bioavailable at least 1 minute to about 60 minutes before the nucleoside analog drugs, DEC or 5AZA. In one embodiment the THU or THU derivative may be bioavailable from 1 minute to about 15 minutes or 15 minutes to 30 minutes, 30 minutes to 45 minutes, 45 minutes to 60 minutes before DEC or 5AZA.

DESCRIPTION OF THE DRAWINGS

FIG. 7 is a graphical representation of the DCK and UCK2 expression levels that correlate with DEC and 5AZA sensitivity respectively.

FIG. 9. is a graphical representation of the efficacy of THU-DEC 3x/wk. alternating with THU-55AZA 3x/wk. in xenotransplant models of patient-derived AML

DETAILED DESCRIPTION

Figure 1:
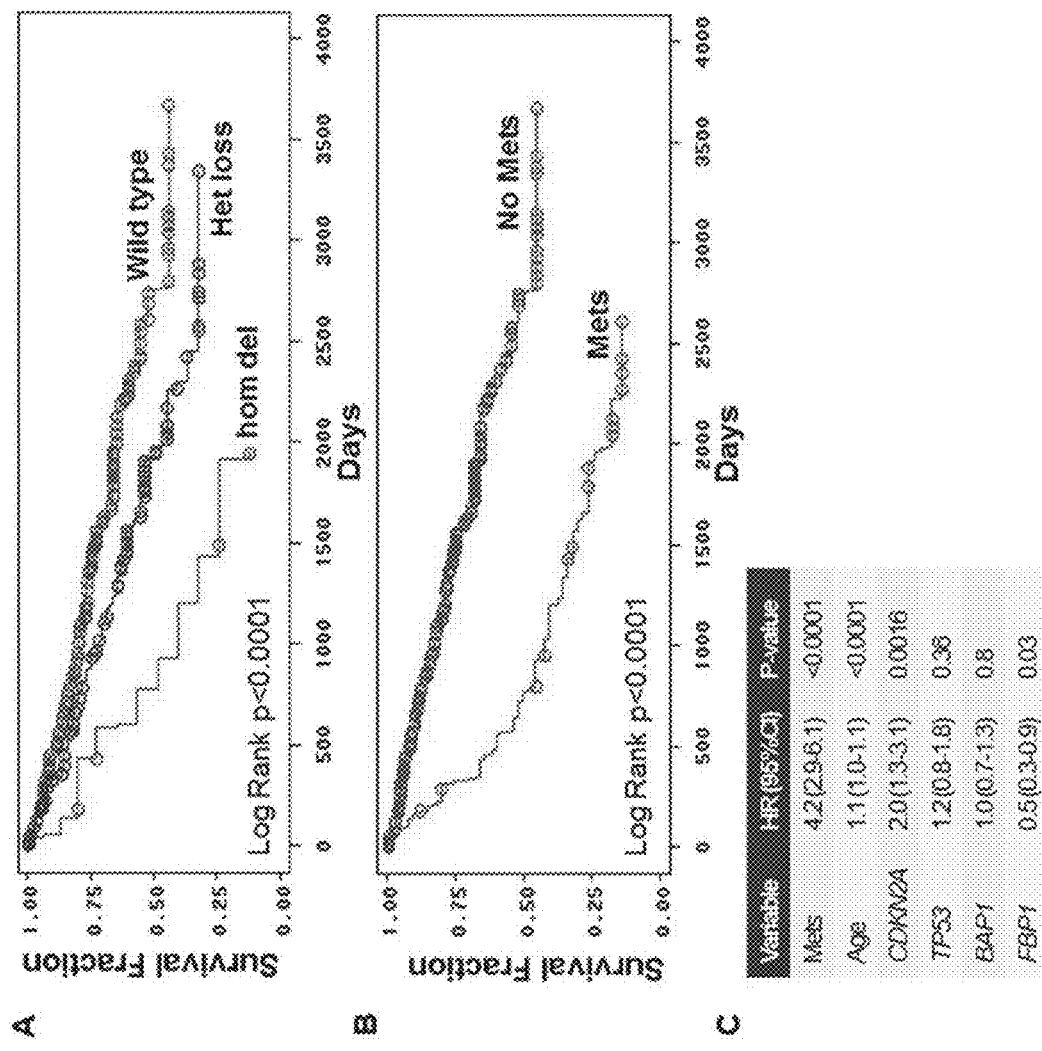
FIG. 1 is a graphical representation of CDKN2A and TP53 deletion/mutations that are prognostic in Renal Cell Carcinoma (RCC).

The present disclosure relates to compositions that contain a nucleoside analog drug in combination with a potent cytidine deaminase inhibitor and pharmaceutically acceptable excipient. The nucleoside analog drug present in the compositions can be any known nucleoside deoxycytidine analog drug that are also DNA demethylating agents including but not limited to DEC, 5AZA, gemcitabine, etc.

The term "nucleoside analogues" refer to any nucleoside that contain a nucleic acid analog and a sugar which upon phosphorylation act as a metabolite inhibitor. Specifically the nucleoside analog in this disclosure refers to cytidine analogs including but not limited to DEC with unmodified sugar and 5AZA. DEC (5-5-aza-2'-deoxycytidine) mimics a natural component of DNA and is relatively unique amongst the large family of nucleoside analogue drugs in that it can irreversibly bind to and deplete the enzyme DNA methyl transferase 1 (DNMT1), and also that the unmodified sugar does not terminate DNA chain elongation, enabling depletion of DNMT1 without cytotoxicity. In cancer cells, DNMT1 depletion by the drug DEC prevents the repression of differentiation genes and renews the differentiation of the cancer cells—the abnormal growth of the cancer cells is caused by a block in their normal differentiation process, which is relieved by DEC. Of special note, DNMT1 depletion in normal stem cells increases their self-renewal; that is, DNMT1 depletion increases the number of normal stem cells—the opposite of its effects on cancer cells. Therefore, DNMT1 depletion by DEC could be an effective and very safe, well-tolerated cancer therapy.

In one embodiment of the invention, the pharmacologic objective of a non-cytotoxic therapy, defined as treatment that does not induce cytotoxicity (apoptosis) of normal dividing cells, is to maximize the time-above-threshold concentration of DEC or 5AZA for depleting DNMT1 (≥0.05-0.2 µM for DEC, ≥0.5-2 µM for 5AZA) in vivo, while avoiding high peak levels (≥0.5-1 µM for DEC, ≥5-10 µM for 5AZA) that damage DNA. This low $C_{max}$ but extended $T_{max}$ exposure will also be produced in solid tissues, into which there is minimal even negligible distribution of current formulations of DEC and 5AZA, because of high CDA expression in solid tissues including the liver, kidneys, intestines and brain. The DNMT1-depleting effect of DEC or 5AZA in the present disclosure is contemplated to be intermittent because continuous exposure to DEC or 5AZA may cause accumulation of DEC or 5AZA in normal cells to levels that induce cytotoxicity. For example the currently known route of administration, regimens, and formulations of DEC or 5AZA can produce high peak levels of the drug that are known to kill normal cells in sensitive tissues such as the bone marrow through cytotoxicity but produce very brief time-above-threshold concentrations for depleting DNMT1 in the bone marrow but especially in solid tissues which highly express CDA. Also, the currently known route of administration, regimens, and formulations of DEC or 5AZA do not increase and distribute exposure times to increase depletion of DNMT1 while avoiding the continuous or sustained exposures that result in accumulation of DEC or 5AZA in normal bone marrow cells to levels that cause cytotoxicity. Instead, these current approaches mimic traditional regimens with pulse-cycled administrations intended for cytotoxic treatment intents. Importantly, the destruction of DEC and 5AZA by the enzyme cytidine deaminase (CDA) produces an abbreviated half-life in vivo of <20 minutes (despite an in vitro half-life of 5-9 hours) (Liu, Z., et al. 2006 Rapid Common Mass Spectrum 20:1117-1126); and this drastic reduction in half-life is a significant barrier to effective in vivo translation of in vitro observations, especially for solid tissue cancers which reside in tissues which intrinsically express high levels of CDA. High peak levels of DEC or 5AZA in the plasma and bone marrow also result from pharmacogenomic variation in CDA (Gilbert, J. A., et al. 2006 Clin. Cancer Res 12, 1794-1803; Kirch, H. C., et al. 1998 Exp. Hematol. 26, 421-425; Yue, L., et al. 2003 Pharmacogenetics 13, 29-38) that produces large inter-individual variation in pharmacokinetics (PK) and clinical effects. Also, malignant cells can develop resistance by destroying DEC with CDA (Ohta, T., et al. 2004 Oncol Rep 12:1115-1120; Hubeek, I., et al. 2005 Br J Cancer 93:1388-1394; Huang, Y., et al. 2004 Cancer Res 64:4294-4301) and the malignant cells may find sanctuary from DEC therapeutic effects by residing in tissues with high levels of CDA (Ebrahem, Q., 2012 Oncotarget 3(10):1137-45).

To address these multiple fundamental pharmacologic limitations of DEC and 5AZA, an oral route of administration of DEC or 5AZA in combination with the CDA inhibitor THU is preferred herein. Such oral administration of DEC or 5AZA in combination with THU substantially decreases peak levels compared to current parenteral administration routes while substantially increasing the time-above-threshold concentrations for depleting DNMT1; the oral administration enables chronic, frequent but not daily (i.e., metronomic) therapy to sustain life-long therapeutic effects, while allowing cell division and avoiding cytotoxicity; the oral combination administration enables distribution of DEC or 5AZA into solid tissues which are sites of cancers and eliminates cancer cell sanctuary in CDA-rich organs such as the liver. In brief; the combination enables treatment of solid tissue cancers. Moreover, the oral administration facilitates wide-spread use of the drugs across the globe. Cytidine deaminase (CDA) is an enzyme that is highly expressed in the liver and intestine and rapidly destroys DEC and 5AZA within the body. In humans, the CDA gene is subject to non-synonymous single nucleotide polymorphisms which produce variants of cytidine deaminase that have differences in enzymatic activity of 3-fold or more (Gilbert, J. A., et al. 2006 Clin Cancer Res 12, 1794-1803; Kirch, H. C., et al. 1998 Exp Hematol 26, 421-425; Yue, L., et al. 2003 Pharmacogenetics 13, 29-38).

THU is known to inhibit the enzyme Cytidine deaminase or CDA and has many desirable characteristics including but not limited to—exhibiting a benign toxicity profile, well-characterized PK, ability to prevail over the intestinal and liver first-pass barriers to oral bioavailability of DEC and 5AZA, producing more predictable effects of a DEC or 5AZA dose from one individual to other, increasing the time-above threshold concentration of DEC or 5AZA for depleting DNMT1, removing the sanctuary sites for malignant cells from DEC or 5AZA therapeutic effects, etc. Hence, in one embodiment the invention provides a composition for oral administration wherein the composition comprises about DEC from about 1-10 mg/m$^2$, or 5AZA in amounts ranging from 10-100 mg/m$^2$, together with the CDA inhibitor THU in amounts ranging from about 400 mg/m$^2$ to about 500 mg/m$^2$. Although the CDA inhibitor used in the composition of the present disclosure is THU, a person skilled in the art may appreciate the fact that other CDA inhibitors such as zebularine may be used instead of THU. In some other embodiment the CDA inhibitor used in the treatment composition may be a commonly known THU derivative such as 2'-fluorinated tetrahydrouridine derivatives synthesized as inhibitors of CDA and described in Ferraris et al. 2014 J Med Chem. 57(6):2582-88 or U.S. Pat. No. 8,329,665 or EP2447272.

Since malignant cells can develop resistance to combination of DEC-THU by shifting pyrimidine metabolism from salvage by DCK to salvage by UCK2, or develop resistance to combination 5AZA-THU by shifting pyrimidine metabolism from salvage with UCK2 to salvage with DCK, both drugs are contemplated to be used alternately or sequentially, to logically address their respective mechanisms of resistance. In another embodiment administration of the composition results in a plasma concentration of DEC of about 0.05 to about 0.5 µM or a concentration of 5AZA of about 0.5 to about 5 µM. In yet another embodiment, a composition is administered once a week or once every two weeks to patients suffering from metastatic cancer. In still another embodiment, the composition is administered between once to three times per week to patients with cancer. In some embodiment, a composition of the invention is administered between once every two weeks to as often as three times per week in patients at risk of developing hematological or solid malignancy, or at risk of having a relapse in a previous diagnosis of hematological or solid malignancy.

5AZA incorporates to a larger extent into RNA than DNA, the incorporation of which results in the inhibition of the protein production. When it incorporates into DNA it covalently binds with DNA methyltransferases that prevent DNA synthesis and subsequent cytotoxicity. In a preferred embodiment the DEC and 5AZA used in the composition for oral administration is a free drug form that are free of salts.

In one embodiment, the disclosure provides a composition for oral administration in the form of a pill, comprising THU and DEC or THU and -5AZA, wherein the THU or 'THU derivative (2'-fluorinated tetrahydrouridine derivatives) is released more quickly than the DEC or 5AZA. It will be appreciated by one skilled in the art that such differential and/or dual release of the drugs of the present disclosure may be effectuated by any known means in the art. The 'differential or dual release' refers to the release at different time points of 'a drug' in a pill containing more than one drug, and/or bioavailability of the drugs at different time points after ingestion. In a differential release formulation for example, the THU might be subject to a faster dissolution rate, or the THU might be located at the surface of the pill, while the DEC or 5AZA is located inside the pill. Because of either the location of THU or the coating or embedding of THU in a polymer or suitable vehicle the THU or THU derivative is bio-available about 1 minute to about 180 minutes before the DEC or 5AZA, in another, about 15 to about 60 minutes before the DEC or 5AZA, in another, about 30 or 60 minutes before the DEC or 5AZA. The THU may also be administered separately, in succession with THU first, then DEC or 5AZA. The term "bio-available", as referred to herein, refers to when the active agent (THU or DEC or 5AZA) can be absorbed and used by the body. "Orally bio-available" indicates that the agent has been taken by mouth and can be absorbed and used by the body.

In another embodiment the composition for oral administration may be a single pill (is also used herein as 'capsule or tablet') that comprises both nucleoside analog drugs, DEC and 5AZA in addition to THU or THU derivative and at least one pharmaceutically acceptable excipient. In this embodiment the DEC or 5AZA and THU are differentially located on the said pill so that THU or THU derivative is bioavailable at least about 1 minute to about 180 minutes before DEC or 5AZA. In this embodiment the drugs, DEC and 5AZA may each exist as either coated or embedded microspheres or microparticles that facilitate the release of the drugs after the THU or THU derivative. This composition comprising both cytidine analog drugs is administered to patient at defined time periods such as between once to three times per week to patients with aggressive and refractory cancer. In yet another embodiment, this composition is administered between once every two weeks to as often as three times per week in patients at risk of developing hematological or solid malignancy, or at risk of having a relapse in a previous diagnosis of hematological or solid malignancy.

The term "pharmaceutically acceptable excipient", as used in the composition refers to carriers and vehicles that are compatible with the active ingredient (for example, a compound of the composition) of a pharmaceutical composition of the invention (and preferably capable of stabilizing it) and not deleterious to the subject to be treated. For example, solubilizing agents that form specific, more soluble complexes with the compounds of the invention can be utilized as pharmaceutical excipients for delivery of the compounds. Suitable carriers and vehicles are known to those of extraordinary skill in the art. The term "excipient" as used herein will encompass all such carriers, adjuvants, diluents, solvents, or other inactive additives. Suitable pharmaceutically acceptable excipients include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical compositions of the invention can also be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like, which do not deleteriously react with the active compounds of the invention.

In another embodiment, the composition of the invention is stored with a desiccant. This could serve to extend the shelf-life of a composition of the invention and facilitate its distribution and use on a global scale.

The term "treating", as used herein, refers to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

Pharmaceutical Compositions

The pharmaceutical compositions of this disclosure can be prepared as described in U.S. application Ser. No. 13/141,669 (issued as U.S. Pat. No. 9,259,469) and Ser. No. 13/414,546 (issued as U.S. Pat. No. 9,265,785), incorporated herein in its entirety. In an embodiment, pharmaceutical compositions and non-toxic dosage forms of the invention comprise about 0.1 to about 0.5 mg/kg CDEC or 1 to about 5 mg/kg of 5AZA and about 10 to about 50 mg/kg THU and a pharmaceutically acceptable excipient, in relative amounts and formulated in such a way that a given pharmaceutical composition or dosage form releases the repression of differentiation pathways in the tumor cell or decreases the aberrant repression of differentiation-related genes in the tumor cell. The therapeutically effective amount of the pharmaceutical compositions and dosage forms of the invention may represent or result in one or more of the following: (i) peak levels of DEC or 5AZA in the plasma of patients that are below thresholds above which there is damage to DNA in normal dividing cells sufficient to cause apoptosis (cytotoxicity), (ii) exposure times sufficient to deplete DNMT1 in cancer cells that are extended to hours from minutes (5 to 20-fold extension of the Tmax) (DEC or 5AZA alone have plasma exposure times of minutes) but are nonetheless below thresholds that cause intra-cellular levels of DEC or 5AZA to accumulate to levels that induce damage to DNA in normal dividing cells sufficient to cause apoptosis (cytotoxicity). In short, exposure time optimized for non-cytotoxic depletion of DNMT1 (iii) a 5 to 20-fold increase in the oral bioavailability of DEC or 5AZA, (iv) Distribution of DEC or 5AZA into CDA-rich tissues in which cancer cells otherwise find sanctuary from DEC or 5AZA treatment effects. This is the same principle underlying oral bioavailability, that is, the ability of DEC or 5AZA to now distribute through the intestines and liver, (v) induce expression of genes and proteins necessary for cell cycle exits by differentiation (p53/p16-independent cell cycle exits) by cancer cells, and (v) Non-cytotoxic mechanism of action, that spares normal dividing cells. Avoidance of toxicity in this way facilitates frequent intermittent treatment to increase the fraction of the cancer exposed to DNMT1-depleting effects.

For example, in some embodiment, the pharmaceutical compositions and dosage forms of the invention comprise about 1 to about 5 mg/kg 5AZA or 0.1 to about 0.5 mg/kg of DEC and about 10 to about 50 mg/kg THU and a pharmaceutically acceptable excipient, in relative amounts and formulated in such a way that a given pharmaceutical composition or dosage form releases the repression of differentiation pathways in the tumor cell or decrease the aberrant repression of differentiation-related genes in the tumor cell.

The pharmaceutical composition or the dosage forms may also include additional active agent including chemotherapeutic agents known in the art. The pharmaceutical compositions may also be administered alone or in combination with other known compositions for treating cancer in a mammalian subject. The term "in combination" may include simultaneous or sequential administration of the composition of this disclosure. The sequential administration may include administration of the disclosed treatment composition followed by any known composition or vice-versa.

The administration of the compositions may be carried out in single or multiple doses. In general, the therapeutically-effective compounds of this disclosure are present in such dosage forms at concentration levels ranging from about 5.0% to about 70% by weight. In some embodiments a subject requiring treatment of tumor may receive a tablet or capsule containing 10 mg/kg of THU and 0.2 mg/kg of DEC or 2 mg/kg of 5AZA twice weekly on consecutive days or once a week or once in 3 days for about a week or two weeks.

To enable differential release of THU or THU derivative and the nucleoside analog drugs, a sustained release composition wherein the active component is derivatized with differentially degradable coatings e.g., by microencapsulation, multiple coatings may be formulated. In some embodiments nanoparticles of the pharmaceutical composition can be prepared as described in U.S. Published application Ser. No. 14/046,343, which is incorporated here in its entirety. These compositions ensure that THU is bioavailable about 1 minute to about 180 minutes before DEC and/or -5AZA. In another embodiment the micro or Nano formulations ensure that the THU is bioavailable about 15 to about 60 minutes or 30 to about 60 minutes before DEC and/or -5AZA.

The compositions of the present disclosure may also additionally include other agents that reduce the rate by which the active compounds will decompose. Such agents may include stabilizers including but not limited to antioxidants, ascorbic acid, pH buffers or salt buffers.

Predictive Biomarkers

Developing "predictive or companion" biomarkers to guide treatment selection is a powerful and effective tool in selecting a meaningful individualized treatment regimen such as the dosage and schedule for any subject in need of treatment. Accordingly a predictive biomarker in the form of an enzyme profile is measured during the treatment regimen to assist the treating physician determine the appropriate treatment regimen for the subject. DNA synthesis and renewal of genetic material are essential for cell proliferation, and high expression of the pyrimidine salvage enzyme DCK is a pan-cancer hall mark of proliferation. Accordingly, radio-labeled nucleoside analogs may be employed for imaging tumor proliferation through the salvage pathway of DNA synthesis. 1-(2'-deoxy-2'-[$^{18}$F]-fluoro-β-D-arabinofuranosyl)cytosine (TFAC), which like DEC, is a deoxycytidine analogue, is one such radio-tracer. Since active DEC needs to be activated by DCK to produce its DNMT1-depleting effect, cancer DCK expression reliably predicts sensitivity to DEC, across the full spectrum of cancer histology and genetics. Accordingly, TFAC-Positron emission tomography (PET) may be employed to measure DCK-dependent cancer cell proliferation.

In some embodiment the predictive bioassay may be conducted before, during and after the treatment with the disclosed compositions. The assay may be conducted to select the appropriate treatment regimen. For example if the assay before or during treatment indicates a high FAC uptake which correlate with the response to oral THU-DEC, the treating physician may continue to prescribe a pill or tablet that comprises THU-DEC. If the FAC uptake is low or decreasing in the context of increasing tumor size indicating the dominance of cancer cells that use the alternative pyrimidine metabolism enzyme, UCK2—a mechanism of resistance to DEC, then the physician may prescribe the tablet or capsule comprising THU-5AZA.

Figure 8:
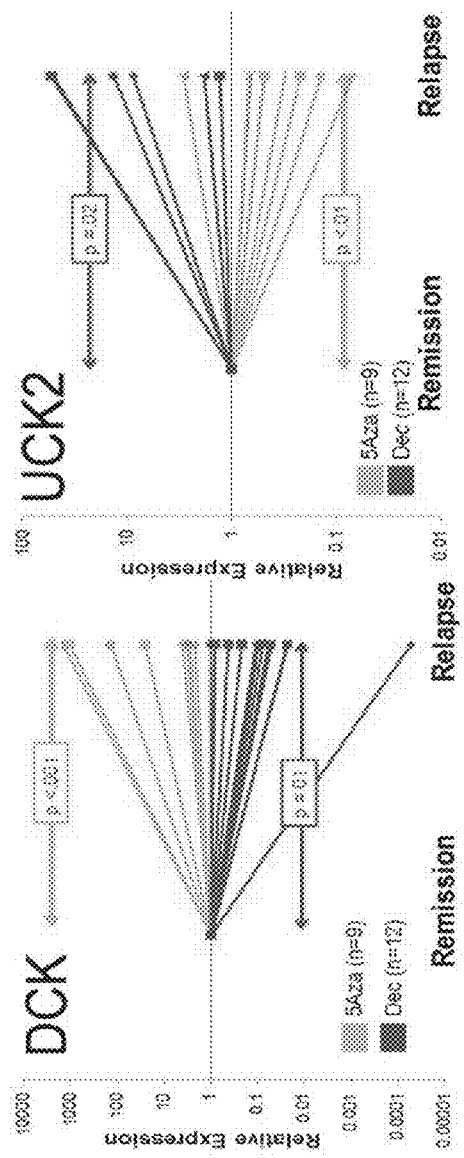
FIG. 8 is a graphical representation at relapse of the MDS/AML cells from patients treated with Dec having lower DCK and higher UCK2 levels and vice-versa in 5-Aza treated patients.

Critically, these measurements do not just provide scientific insight into mechanisms of resistance, but guide application of rational clinical measures to overcome resistance and extend response: (i) failure to achieve molecular-PD in the context of no side-effects of this non-cytotoxic therapy can guide rational increases in the dosage or frequency of oral THU-DEC (FIG. 9). (ii) Resistance with re-increasing variant allele frequency burden concurrent with loss of molecular-PD and shift in pyrimidine metabolism enzymes can guide rational switch in therapy to oral THU-5AZA (FIG. 9). Optimal application will likely incorporate oral THU-DEC administered for one alternating with oral THU-55AZA administered the next week on a chronic, long-term basis (FIGS. 7-9).

Methods of Treatment

In one embodiment a pill comprising the treatment composition of the present disclosure may be administered to a cancer patient in need of treatment. The cancer may be a solid or liquid cancer or may be an aggressive and refractory cancer of any known tissues in a subject. The treatment composition of the present disclosure may also be effective in treating hematological malignancies or blood disorders such as but not limited to sickle cell disease, hemoglobinopathies, thalassemias or any associated conditions that are elaborated in U.S. patent application Ser. No. 13/414,546, now issued as U.S. Pat. No. 9,265,785, incorporated herein in its entirety. 'Treatment or treating' refers to any known physical and/or biochemical and/or molecular changes in the cancer tissue. For example treatment may refer to amelioration of a tumor size or a known cancer biomarker protein such as the level of DNMT1 in normal and malignant cells or may be molecular, as in de-repression of specific differentiation genes or all of the above. The method of treatment includes assaying a predictive biomarker before, during or after the treatment. The predictive biomarker may inform the treating physician the appropriate dosage and schedule to prescribe to the patient. For example patients may receive the drugs of the present disclosure as follows: oral THU 10 mg/kg, followed by oral DEC 0.2 mg/kg 60 minutes after the THU, twice weekly on consecutive days. The treatment may include administering a pill comprising THU-DEC or THU-5AZA or a pill containing both DEC and 5-5AZA, wherein the THU or THU derivative is bioavailable about 1 minute to about 180 minutes or 15 to about 180 minutes before DEC and/or 5AZA.

The treatment method may include the administration of a first composition comprising DEC, THU or a THU derivative and at least one pharmaceutically acceptable excipient followed by days or weeks apart by alternate administration of a second composition comprising 5AZA, THU or a THU derivative and at least one pharmaceutically acceptable excipient. This sequential or alternate treatment method may be followed for several weeks to several months.

In some aspects the method of treatment includes an additional therapeutic modality including but not limited to radiation therapy or a cytotoxic chemotherapy agent such as an anti-metabolite, doxorubicin, HDAC inhibitors, anti-viral agents, anti-retroviral agent or any combination of these agents as described in detail in U.S. Published application Ser. No. 14/046,343, incorporated here in its entirety.

EXAMPLES

The following examples are provided for illustrative purposes only and are not intended to limit the scope of the invention.

Example 1

A Need for Treatments Mechanistically Distinct from Current Options

Historically, most drugs evaluated in RCC attempted to terminate proliferation using the p53/p16 apoptosis system (cytotoxicity). For decades, such treatments proved to be toxic and ineffective because RCC cells, like most cancer cells, are apoptosis-resistant relative to normal cells, through genetic abnormalities in key p53/p16-system genes such as CDKN2A. The first drugs approved by the FDA to treat RCC inhibited signaling pathways (e.g., AKT/mTOR) that stabilize MYC protein that is the master coordinator of cell growth and division. Thus, these drugs impede RCC growth directly through effects on MYC protein and also indirectly, by inhibiting angiogenesis needed to support RCC growth. Although such therapies are a clear advance, durable response is rare (median survival 18-30 months), and p53/p16 alterations still impact response, robust to multi-variate analyses (FIG. 1). Moreover, responses in $2^{nd}$ or $3^{rd}$ line are substantially less durable than responses in $1^{st}$ line, suggesting some overlap in mechanisms of resistance to approved drugs. It is thus indicated and appropriate to evaluate mechanistically distinct treatments that explicitly use pathways other than p53/p16 to terminate RCC cell growth and division.

PBRM1 Inactivation in RCC and Epithelial Differentiation Therapy

Figure 2:
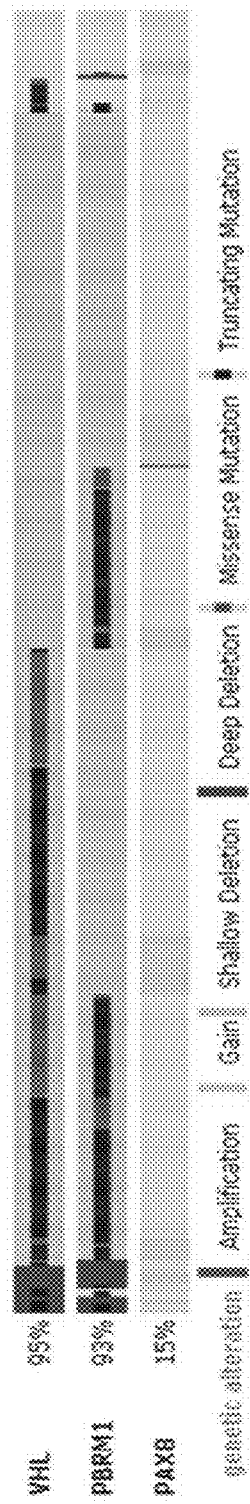
FIG. 2 is a graphical representation of the genes, VHL, PBRM1 and Pax8, amplified or deleted in RCC.
Figure 3:
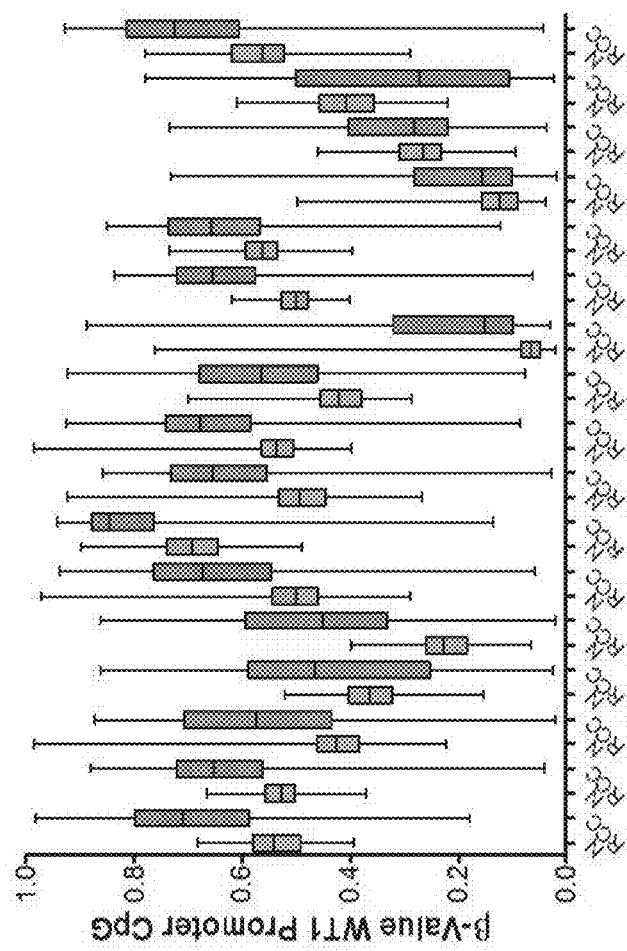
FIG. 3 is a graphical representation showing the hypermethylated WT1 promoter CpG in RCC compared to non-paired non-cancerous kidney.
Figure 4:
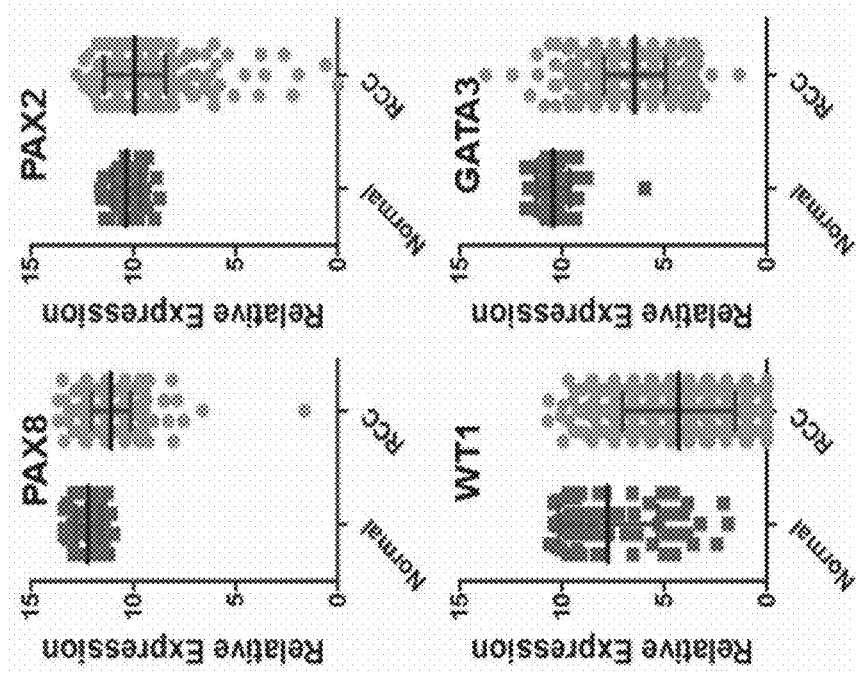
FIG. 4 is a graphical representation of the high expression of differentiation drivers and paradoxically epigenetic repression of key epithelial differentiation target genes (e.g., WT1 and GATA3) in RCC.
Figure 5:
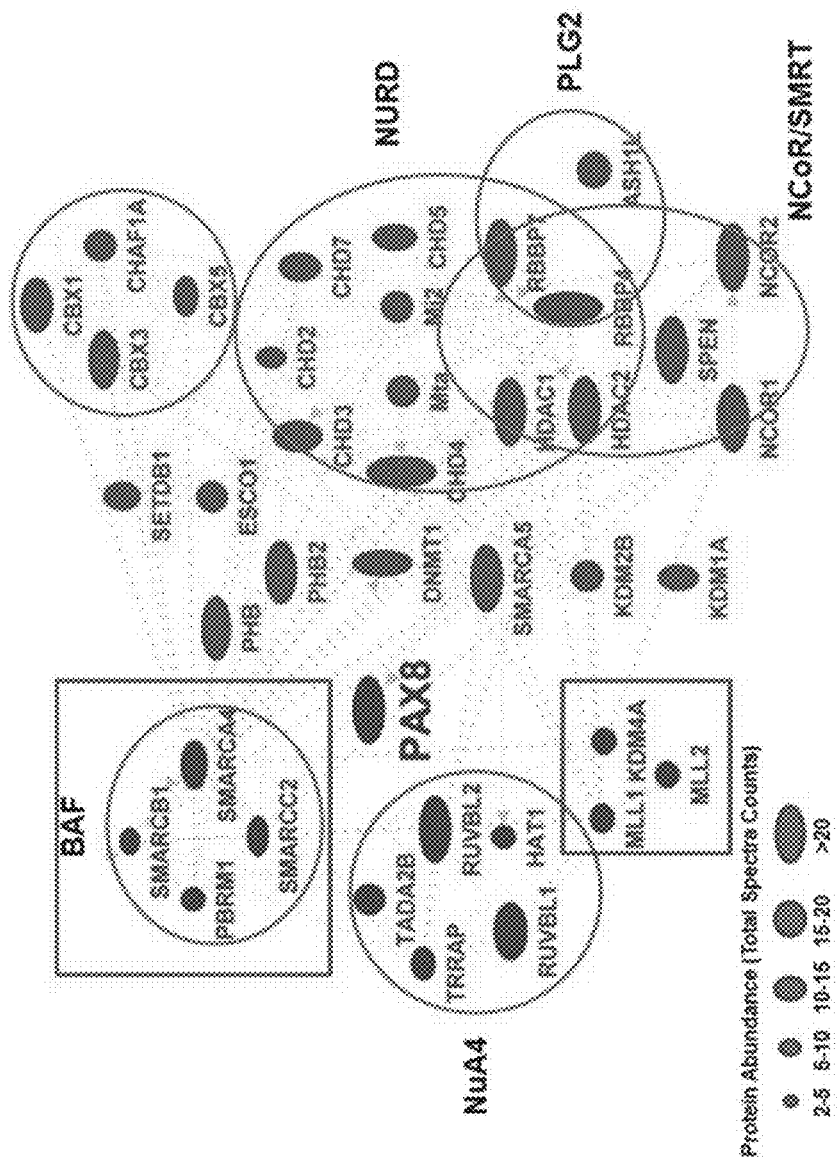
FIG. 5 is a comprehensive documentation of CoActivator and CORepressor Interactions of Pax8 by LC/MSMS.
Figure 6:
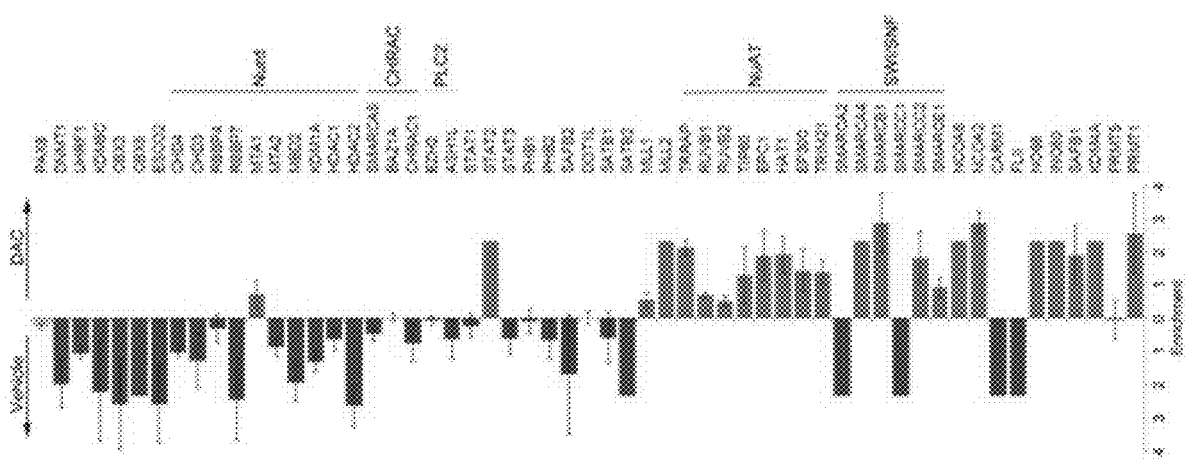
FIG. 6 is graphical representation of the PAX8 interactions towards CoActivators and CoRepressors due to DNMT1 depletion by non-cytotoxic concentrations of DEC.

An unexpected revelation from RCC genomic studies is essentially universal inactivating alterations of genes for coactivator subunits, especially PBRM1, but also others (SETD2, SMARCC1, SMARCA2, ARID1A) (FIG. 2). These observations are recent, and the pathway function of these coregulators in normal kidney cells, or the pathways by which loss of function conferred clonal advantage, were unknown. We conjectured that a possibly connected observation was epigenetic suppression of key epithelial terminal differentiation genes (e.g., GATA3, WT1) in RCC (FIGS. 3, 4). This epigenetic repression of late-differentiation genes was particularly intriguing because RCC cells express un-mutated master transcription factors that drive epithelial differentiation (e.g., PAX8, PAX2) at relatively preserved mRNA and high protein levels (FIG. 4). Another pertinent observation was correlation of increased chromatin repression marks with worse prognosis in multiple RCC studies. In the last funding cycle we connected these observations experimentally, discovering that PBRM1/BAF mediates transcription activation by PAX8, a master driver of mesenchymal-epithelial transition11-16 that is highly expressed in RCC17-22. PBRM1 loss causes unbalanced recruitment to PAX8 of corepressor counterparts to PBRM1/BAF (e.g., DNMT1), repressing instead of activating proliferation-terminating epithelial-differentiation target genes (FIG. 5). Importantly, inhibiting these specific corepressors (e.g., DNMT1) restored expression of multiple PAX8 target genes, renewing epithelial differentiation and physiologic, p53/p16-independent cell cycle exits (FIG. 6).

Example 2

A Need for Mechanism-Based Predictive Biomarkers

Figure 10:
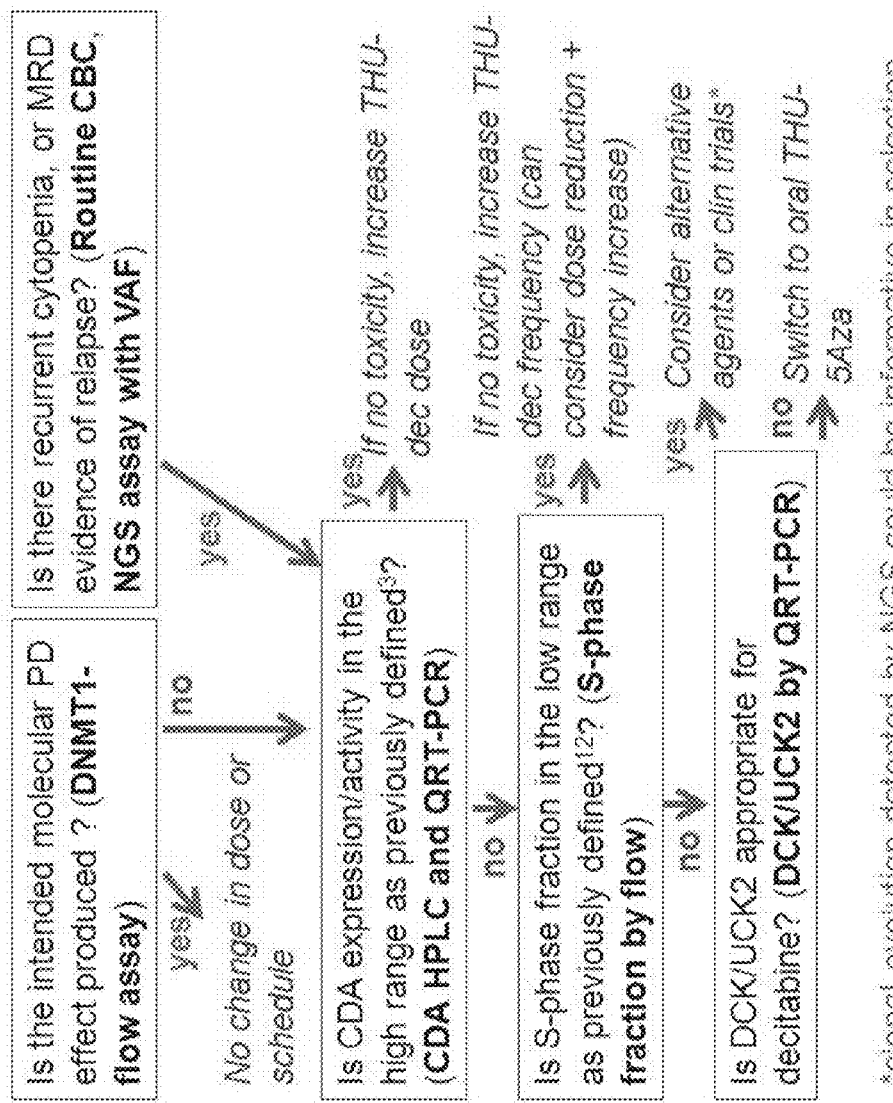
FIG. 10 is a flow chart showing how the biomarkers can guide logical measures to extend the response to drugs and salvage relapse.

DNA synthesis and renewal of genetic material are essential for cell proliferation, and high expression of the pyrimidine salvage enzyme DCK is a pan-cancer hall mark of proliferation. Accordingly, radio-labeled nucleoside analogs have been developed for imaging tumor proliferation through the salvage pathway of DNA synthesis. 1-(2'-deoxy-2'-[18F]-fluoro-β-D-arabinofuranosyl)cytosine (FAC), like Dec a deoxycytidine analogue, is one such radio-tracer. It has been documented that similar to Dec, however, FAC did not adequately distribute into solid tissues such as the liver and kidneys, because of rapid deamination by CDA. It was then found that THU-FAC (TFAC) co-injection solves this problem, producing high FAC uptake in hepatocellular cancer against the background liver in a woodchuck animal model of viral infection induced primary hepatocellular cancer. As shown in FIG. 10 the use of predictive biomarker assay will help determine whether the frequency or dose of the THU-Dec should be increased.

In this way, TFAC-PET could suggest rational salvage therapy. If validated, it could also have a role in upfront treatment selection between THU-Dec versus THU-5Aza. Additionally, it could be that TFAC-PET does capture an aspect of RCC biology that correlates well with response and outcomes to other RCC drugs (sunitinib etc.). In other words, it is conceivable that TFAC-PET could fulfill the broad predictive biomarker role that FDG-PET has not been able to meet. Potential utility demonstrated here can justify evaluation for such a broader purpose.

Example 3

Treatment Resistant Malignant Cells in Patients Treated with DEC Upregulate UCK2 and Downregulate DCK and Vice-Versa in Patients Treated with 5AZA Bone marrow aspirate specimens were obtained from patients before and at the time of relapse while on treatment with DEC or 5AZA, and expression of the pyrimidine metabolism enzymes DCK and UCK2 was measured by quantitative real-time PCR. As shown in FIG. 8 during relapse MDS/AML cells from patients treated with Dec have lower DCK and higher UCK2, and vice versa in 5Aza treated patients.

Example 4

Non-Cytotoxic Treatment Using THU-DEC 3×/Wk. Alternating with THU-5AZA 3×/Wk. Strikingly Extends Response Compared to DEC Alone, or THU-DEC Alone, in Xenotransplant Models of Patient-Derived AML Primary AML cells ($1\times10^6$ cells) from the bone marrow of a patient with AML were xenotransplanted into NSG mice. Five days after the inoculation, mice were treated with vehicle, DEC alone at 0.2 mg/kg subcutaneous 3×/week, THU-DEC (THU 8 mg/kg with DEC 0.1 mg/kg) subcutaneous 3×/week or THU-DEC 3×/week alternating with THU-5AZA 3×/week (THU 8 mg/kg with 5AZA 1 mg/kg). n=5 per treatment group. As evident from FIG. 9 the alternating regimen of THU-Dec with Thu-5Aza significantly increases the survival probability in these xenotransplant models of patient-derived AML.

What is claimed is:

1. A method for treating a cancer or a blood disorder in a subject, the method comprising:
    administering a first composition to the subject comprising decitabine, tetrahydrouridine and a pharmaceutically acceptable carrier,
    administering a second composition to the subject comprising 5-azacytidine, tetrahydrouridine and a pharmaceutically acceptable carrier,
    wherein the first and the second compositions are administered to the subject alternately.

2. The method of claim 1 wherein the first composition administered to the subject comprises about 1 to about 10 mg/m$^2$ of decitabine and about 400 to 500 mg/m$^2$ of tetrahydrouridine.

3. The method of claim 1, wherein the second composition administered to the subject comprises about 10 to about 100 mg/m$^2$ of 5-azacytidine and about 400 to 500 mg/m$^2$ of tetrahydrouridine.

4. The method of claim 1, wherein administration of the first and second compositions result in a peak decitabine plasma concentration of less than about 0.5 µM and a peak 5-azacytidine plasma concentration of not more than 5 µM in the subject.

5. The method of claim 1, wherein the tetrahydrouridine in the first and second composition is bio-available about 1 minute to about 180 minutes before decitabine or 5-azacytidine.

6. The method of claim 1, wherein the tetrahydrouridine in the first and second compositions is a 2'-fluorinated tetrahydrouridine derivative and is bio-available about 15 minutes to about 180 minutes before decitabine or 5-azacytidine.

7. The method of claim 1, wherein the first composition is present in a first pill and the second composition is present in a second pill.

8. The method of claim 1, wherein the cancer is a benign, metastatic or refractory cancer of any tissue.

9. The method of claim 1, wherein the blood disorder is sickle cell disease, thalassemia or hemoglobinopathy.

10. The method of claim 1, wherein the first and the second composition are administered after measuring a predictive biomarker in the subject.

11. The method of claim 10, wherein the measurement of the predictive biomarker includes the deoxycytidine kinase levels in the subject.

12. The method of claim 1, wherein the subject is a mammal.

13. The method of claim 1, wherein the 5-azacytidine and the tetrahydrouridine are differentially located in the second composition, and wherein the tetrahydrouridine is bio-available about 1 minute to about 180 minutes before the 5-azacytidine.

14. The method of claim 1, wherein the second composition comprises about 10 to about 100 mg/m$^2$ of 5-azacytidine and about 400 to 500 mg/m$^2$ of tetrahydrouridine, and wherein the tetrahydrouridine is bio-available about 1 minute to about 180 minutes before the 5-azacytidine.

15. The method of claim 1, wherein the second composition comprises about 10 to about 100 mg/m$^2$ of 5-azacytidine and about 400 to 500 mg/m$^2$ of tetrahydrouridine, wherein the second composition is in form of a pill or tablet or capsule, wherein the tetrahydrouridine is located on the surface and the 5-azacytidine is located inside the pill or tablet or capsule, and wherein the tetrahydrouridine is bio-available about 1 minute to about 180 minutes before the 5-azacytidine.

* * * * *